(12) United States Patent
Bancalari et al.

(10) Patent No.: US 9,778,141 B2
(45) Date of Patent: Oct. 3, 2017

(54) VIDEO INSPECTION SYSTEM WITH DEFORMABLE, SELF-SUPPORTING DEPLOYMENT TETHER

(71) Applicant: Siemens Energy, Inc., Orlando, FL (US)

(72) Inventors: Alejandro Bancalari, Casselberry, FL (US); Clifford Hatcher, Jr., Orlando, FL (US); Forrest R. Ruhge, Orlando, FL (US); James P. Williams, Orlando, FL (US); Joshua DeAscanis, Oviedo, FL (US); David Letter, Deland, FL (US); Robert G. Shannon, Oviedo, FL (US)

(73) Assignee: Siemens Energy, Inc., Orlando, FL (US)

( * ) Notice: Subject to any disclaimer, the term of this patent is extended or adjusted under 35 U.S.C. 154(b) by 254 days.

(21) Appl. No.: 14/803,149

(22) Filed: Jul. 20, 2015

(65) Prior Publication Data
US 2015/0338353 A1 Nov. 26, 2015

Related U.S. Application Data

(63) Continuation-in-part of application No. 13/972,000, filed on Aug. 21, 2013, now Pat. No. 9,116,071, and
(Continued)

(51) Int. Cl.
*G01M 15/14* (2006.01)
*G01M 15/02* (2006.01)
(Continued)

(52) U.S. Cl.
CPC ............ *G01M 15/02* (2013.01); *F01D 21/003* (2013.01); *G01M 15/14* (2013.01); *G01N 21/954* (2013.01);
(Continued)

(58) Field of Classification Search
USPC .............................. 73/112.01, 112.02, 112.05
See application file for complete search history.

(56) References Cited

U.S. PATENT DOCUMENTS

| 4,216,802 A | 8/1980 | Bonnes et al. |
| 5,102,221 A | 4/1992 | Desgranges et al. |
| (Continued) | | |

FOREIGN PATENT DOCUMENTS

EP   0907077   4/1999

OTHER PUBLICATIONS

Co-pending utility U.S. Appl. No. 13/971,938, filed Aug. 21, 2013.
(Continued)

*Primary Examiner* — Eric S McCall

(57) ABSTRACT

Non-destructive evaluation optical inspection systems include video cameras or other reflective-photonic optical instruments, such as laser profilometers or 3D white light laser dimensional scanners, which are incorporated in a camera head. The camera head is coupled to a distal end of a self-supporting and shape-retaining elongate deformable deployment tether. The deployment tether is bendable, for insertion through cavities of power generation machines and orientation of the camera head field of view on the internal area of interest. The deployment tether is capable of being deformed repeatedly, for inspection of different areas of interest. In some embodiments, interchangeable camera heads are selectively coupled to the deployment tether, so that a kit or family of different optical inspection instruments are available to carry out multiple types of inspections within a single or multiple types of power generation machinery.

16 Claims, 7 Drawing Sheets

Related U.S. Application Data a continuation-in-part of application No. 13/362,352, filed on Jan. 31, 2012, now Pat. No. 8,713,999, and a continuation-in-part of application No. 13/362,387, filed on Jan. 31, 2012, now Pat. No. 8,922,640, and a continuation-in-part of application No. 13/362,417, filed on Jan. 31, 2012, now Pat. No. 9,057,710, and a continuation-in-part of application No. 14/732,982, filed on Jun. 8, 2015.

(60) Provisional application No. 61/692,393, filed on Aug. 23, 2012, provisional application No. 61/692,409, filed on Aug. 23, 2012.

(51) Int. Cl.

| | | |
|---|---|---|
| *H04N 7/18* | (2006.01) | |
| *H04N 5/225* | (2006.01) | |
| *H04N 5/232* | (2006.01) | |
| *F01D 21/00* | (2006.01) | |
| *G02B 23/24* | (2006.01) | |
| *G01N 21/954* | (2006.01) | |

(52) U.S. Cl.
CPC ....... *G02B 23/2484* (2013.01); *H04N 5/2252* (2013.01); *H04N 5/2253* (2013.01); *H04N 5/23293* (2013.01); *H04N 7/183* (2013.01); *G01N 2021/9544* (2013.01); *H04N 2005/2255* (2013.01)

(56) References Cited

U.S. PATENT DOCUMENTS

| | | |
|---|---|---|
| 5,164,826 A | 11/1992 | Dailey |
| 5,349,850 A | 9/1994 | Young |
| 6,317,387 B1 | 11/2001 | D'Amaddio et al. |
| 6,992,315 B2 | 1/2006 | Twerdochlib |
| 7,068,029 B2 | 6/2006 | Hatcher et al. |
| 7,271,894 B2 | 9/2007 | Devitt et al. |
| 7,489,811 B2 | 2/2009 | Brummel et al. |
| 7,956,326 B1 | 6/2011 | Kychakoff et al. |
| 8,184,151 B2 | 5/2012 | Zombo et al. |
| 8,299,785 B2 | 10/2012 | Bousquet et al. |
| 8,713,999 B2 | 5/2014 | Hatcher |
| 8,922,640 B2 | 12/2014 | Hatcher et al. |
| 2004/0051525 A1 | 3/2004 | Hatcher et al. |
| 2004/0193016 A1 | 9/2004 | Root et al. |
| 2005/0199832 A1 | 9/2005 | Twerdochlib |
| 2005/0200355 A1 | 9/2005 | Hatcher et al. |
| 2005/0288551 A1* | 12/2005 | Callister ............ A61B 1/00082 600/115 |
| 2006/0088793 A1 | 4/2006 | Brummel et al. |
| 2007/0038052 A1* | 2/2007 | Swoyer ................ A61N 1/0551 600/345 |
| 2007/0129604 A1 | 6/2007 | Hatcher et al. |
| 2007/0157733 A1 | 7/2007 | Litzenberg et al. |
| 2007/0296964 A1 | 12/2007 | Nishimura et al. |
| 2009/0312783 A1* | 12/2009 | Whayne ........ A61B 17/320016 606/190 |
| 2010/0305715 A1* | 12/2010 | Mathis ................. A61B 1/2676 623/23.65 |
| 2011/0004157 A1* | 1/2011 | Dewaele ............ A61B 1/00071 604/95.01 |
| 2011/0018530 A1 | 1/2011 | Bousquet et al. |
| 2011/0267428 A1 | 11/2011 | George et al. |
| 2012/0154594 A1 | 6/2012 | Xie et al. |
| 2012/0281084 A1 | 11/2012 | Hatcher et al. |
| 2013/0194412 A1 | 8/2013 | Hatcher et al. |
| 2013/0194413 A1 | 8/2013 | Hatcher et al. |
| 2014/0168420 A1 | 6/2014 | Naderhirn |
| 2014/0259641 A1* | 9/2014 | Brannan ............ A61B 18/1815 29/602.1 |
| 2014/0276739 A1* | 9/2014 | Brannan ............ A61B 18/1815 606/33 |

OTHER PUBLICATIONS

Co-pending utility U.S. Appl. No. 13/362,417, filed Jan. 31, 2012.
Co-pending utility U.S. Appl. No. 13/362,352, filed Jan. 31, 2012, now U.S. Pat. No. 8,713,999 issued on May 6, 2014.
Co-pending utility U.S. Appl. No. 13/362,387, filed Jan. 31, 2012, now U.S. Pat. No. 8,922,640 issued on Dec. 30, 2014.
Co-pending utility U.S. Appl. No. 13/972,000, filed Aug. 21, 2013.
Co-pending utility U.S. Appl. No. 14/732,982, filed Jun. 8, 2015.

* cited by examiner

VIDEO INSPECTION SYSTEM WITH DEFORMABLE, SELF-SUPPORTING DEPLOYMENT TETHER

CROSS-REFERENCE TO RELATED APPLICATIONS

This application is a continuation-in-part of United States utility patent application entitled "System And Method For Visual Inspection And 3D White Light Scanning Of Off-Line Industrial Gas Turbines And Other Power Generation Machinery", filed, Aug. 21, 2013 and assigned Ser. No. 13/972,000; which in turn claims the benefit of United States provisional patent application entitled "Hybrid Scope—Turbine Combustor Hardware Visual Inspection Tooling That Can Also Be Used To Inspect The Row 1 Turbine Blades While They Are On Turning Gear (1-1000 rpm)" filed Aug. 23, 2012 and assigned Ser. No. 61/692,393 and United States provisional patent application entitled "Vision Scope—3D Scanner Tip for Visual Inspection and Measurement" filed Aug. 23, 2012 and assigned Ser. No. 61/692,409; and which is also a continuation-in-part of United States utility patent application entitled "System And Method For Automated Optical Inspection Of Industrial Gas Turbines And Other Power Generation Machinery With Multi-Axis Inspection Scope", filed Jan. 31, 2012 and assigned Ser. No. 13/362,352, now U.S. Pat. No. 8,713,999 and which is also a continuation-in-part of United States utility patent application entitled "System and Method for Automated Optical Inspection of Industrial Gas Turbines and Other Power Generation Machinery with Articulated Multi-Axis Inspection Scope", filed Jan. 31, 2012 and assigned Ser. No. 13/362,387, now U.S. Pat. No. 8,922,640 and which is also a continuation-in-part of United States utility application entitled "System and Method for Automated Optical Inspection of Industrial Gas Turbines and Other Power Generation Machinery", filed on Jan. 31, 2012 and assigned Ser. No. 13/362,417, now U.S. Pat. No. 9,057,710; the entire contents of each of these claimed priority applications is incorporated by reference herein.

This application is a continuation-in-part of United States utility patent application entitled "Method And System For Surface Profile Inspection Of Off-Line Industrial Gas Turbines And Other Power Generation Machinery", filed, Jun. 8, 2015 and assigned Ser. No. 14/732,982, which is a continuation-in-part of United States utility patent application entitled "System And Method For Visual Inspection And 3D White Light Scanning Of Off-Line Industrial Gas Turbines And Other Power Generation Machinery", filed, Aug. 21, 2013 and assigned Ser. No. 13/972,000; which in turn claims the benefit of United States provisional patent application entitled "Hybrid Scope—Turbine Combustor Hardware Visual Inspection Tooling That Can Also Be Used To Inspect The Row 1 Turbine Blades While They Are On Turning Gear (1-1000 rpm)" filed Aug. 23, 2012 and assigned Ser. No. 61/692,393 and United States provisional patent application entitled "Vision Scope—3D Scanner Tip for Visual Inspection and Measurement" filed Aug. 23, 2012 and assigned Ser. No. 61/692,409; and which is also a continuation-in-part of United States utility patent application entitled "System And Method For Automated Optical Inspection Of Industrial Gas Turbines And Other Power Generation Machinery With Multi-Axis Inspection Scope", filed Jan. 31, 2012 and assigned Ser. No. 13/362,352, now U.S. Pat. No. 8,713,999 and which is also a continuation-in-part of United States utility patent application entitled "System and Method for Automated Optical Inspection of Industrial Gas Turbines and Other Power Generation Machinery with Articulated Multi-Axis Inspection Scope", filed Jan. 31, 2012 and assigned Ser. No. 13/362,387, now U.S. Pat. No. 8,922,640 and which is also a continuation-in-part of United States utility application entitled "System and Method for Automated Optical Inspection of Industrial Gas Turbines and Other Power Generation Machinery", filed on Jan. 31, 2012 and assigned Ser. No. 13/362,417, now U.S. Pat. No. 9,057,710; the entire contents of each of these applications is incorporated by reference herein.

BACKGROUND OF THE INVENTION

1. Field of the Invention

The invention relates to video and other reflective-photonic inspection systems for non-destructive internal inspection of power generation machines, such as combustion or steam turbine engines, generators, and other plant equipment for power generation. More particularly, the invention relates to video/camera inspection systems having self-supporting and shape-retaining elongate deformable deployment tethers and a camera head coupled to the deployment tether distal end, for capturing images of internal areas of interest within power generation equipment. The deployment tether is bendable, for insertion through cavities of the power generation machine and orientation of the camera head field of view on the internal area of interest within the machine. The deployment tether is capable of being deformed repeatedly for inspection of different areas of interest within the same machine or in different machines.

2. Description of the Prior Art

Power generation machinery, such as steam or gas turbine engines or generators, are often operated continuously with scheduled inspection and maintenance periods, at which time the machinery is taken off line and shut down. By way of example, a gas turbine engine often will be operated to generate power continuously for approximately 4000 hours, thereupon it is taken off line for routine maintenance, inspection, and repair of any components identified during inspection. Taking a gas turbine engine off line and eventually shutting it down completely for scheduled maintenance is a multi-day project. Some turbine components, such as the turbine rotor section, are operated at temperatures exceeding 1000° C. (1832° F.). The turbine requires 48-72 hours of cooling time to achieve ambient temperature before complete shutdown in order to reduce likelihood of component warping or other deformation. During the shutdown phase the turbine rotor rotational speed is spooled down from operating speed of approximately 3600 RPM to a speed of approximately 120 RPM or less in "turning gear mode" where the rotor is externally driven by an auxiliary drive motor, in order to reduce likelihood of rotor warping. Other turbine components, such as the turbine housing, are also cooled slowly to ambient temperature.

Once the turbine is cooled to ambient temperature over the course of up to approximately 72 hours internal components of the now static turbine can be inspected with optical camera inspection systems. Known optical camera inspection systems employ rigid or flexible optical bore scopes that are inserted into inspection ports located about the turbine periphery. The bore scope is manually positioned so that its field of view encompasses an area of interest within the turbine, such as one or more vanes or blades, combustor baskets, etc. A camera optically coupled to the bore scope captures images of objects of interest within the field of view for remote visualization and archiving (if desired) by an inspector. Rigid tube borescopes are not insertable in twisting or tightly confined cavities within power generation machinery. Flexible tether borescopes are not self-supporting, so the camera field of view stability is disrupted by inadvertent tether movement, such as if the tether inadvertently slips during video inspection. Flexible tether borescopes inadvertently contact internal surfaces within power generation machinery as they are maneuvered through internal machinery passages, risking potential damage to relatively brittle and fragile surfaces, such as thermal barrier coatings on turbine engine blades, vanes or combustor transitions.

Complete turbine inspection requires multiple manual relative repositioning sequences between the camera inspection system viewing port and areas of interest within the turbine by a human inspector. In many field service applications it is also desirable to gather multiple types of visual inspection data, including dimensional and/or surface profile data and/or a general video record of power generation machine internal components during a single pre-teardown inspection cycle. Each type of non-destructive evaluation visual inspection requires a different type of bore scope device/system to perform each specific type of inspection.

SUMMARY OF THE INVENTION

Exemplary embodiments of the invention are directed to non-destructive evaluation optical inspection systems, which employ reflective-photonic instruments, such as video or still cameras of different image resolution, laser profilometers, or 3D white light laser dimensional scanners. The optical instrument is coupled a camera head that is in turn coupled to a distal end of a self-supporting and shape-retaining elongate deformable deployment tether. The deployment tether is bendable, for insertion through cavities of the power generation machine and orientation of the camera head field of view on the internal area of interest within the machine. The deployment tether is capable of being deformed repeatedly for inspection of different areas of interest within the same machine or in different machines. In some embodiments, the inspection instruments are coupled to respective selectively interchangeable camera heads that are selectively coupled to the deployment tether, so that a kit or family of different inspection instruments are available to carry out multiple types of inspections within a single or multiple types of power generation machinery. In some exemplary embodiments, the inspection instrument, such as a video camera, is coupled to a video control system that receives camera video images for further processing.

Exemplary embodiments of the invention feature a video inspection scope system, which includes a self-supporting and shape retaining, elongate deformable tubular deployment tether having distal and proximal ends. The tether constructed of a metallic inner tube, defining a lumen therethrough that is radially circumscribed by a polymeric outer layer that is bonded thereto. A camera head is coupled to the distal end of the deployment tether. A video camera or other photonic-reflective inspection instrument is coupled to the camera head, for capturing video images or other respective images. In some embodiments, a video control system is coupled to the video camera, for receiving camera video images for further processing. In some embodiments, the deployment tether comprises deformable metallic inner tube that is capable of multiple, sequential bending deformations along a common portion, without cracking the inner tube. In some embodiments, the video camera comprises a five mega pixel (5 MP) or greater personal computer, tablet computing device, or smart telephone camera board that is coupled to the video control system via a USB-type cable retained within the tube lumen. In some embodiments a selectively engageable coupling element couples the deployment tether distal end and the camera head, for selectively engaging the tether and camera head to each other, so that a plurality of additional, replaceable camera heads respectively having different reflective-photonic, non-destructive evaluation instruments are coupled to the tether for different types of inspections within the same power generation machine or within different machines.

Other exemplary embodiments of the invention feature a method for internal non-destructive inspection of areas of interest within a power generation machine. The provided power generation machine has areas of interest therein that are in communication with corresponding internal passages. The passages are externally accessible from outside the machine. A video inspection scope is provided, which includes a self-supporting and shape retaining, elongate deformable tubular deployment tether having distal and proximal ends. The tether is constructed of a metallic inner tube, defining a lumen therethrough that is radially circumscribed by a polymeric outer layer that is bonded thereto. A camera head is coupled to the distal end of the deployment tether. A video camera (or other reflective-photonic, optical inspection instrument), is coupled to the camera head, for capturing video images within a camera field of view. A video control system is coupled to the video camera, and receives camera video images for further processing. During the inspection process, a first internal area of interest is inspected within the provided power generation machine by bending the metallic inner tube to conform elongate profile of the deployment tether to a first deformation profile. The bent first profile facilitates insertion of the tether and camera head proximate the first internal area of interest through a corresponding internal passage that is in communication with the area of interest. The first deformation profile deployment tether and camera head are inserted into the corresponding internal passage, so that the camera head is proximate the first area of interest. Movement of the deployment tether proximal end orients the camera field of view to include the first area of interest, and an image of the area of interest is captured by the camera. The captured image is transferred to the video control system.

Additional exemplary embodiments of the invention feature a method for internal non-destructive inspection of areas of interest within a combustion turbine engine having: compressor and turbine sections including therein a rotatable rotor with rows of blades affixed thereto, and rows of stationary vanes interposed between the blade rows; a combustor section interposed between the compressor and turbine sections. The engine has internal passages that are in communication with internal areas of interest within the respective compressor, turbine, and combustor sections, and those passages are externally accessible from outside the engine. A video inspection scope system is provided, having: a self-supporting and shape retaining, elongate deformable tubular deployment tether having distal and proximal ends. The tether is constructed of a metallic inner tube, defining a lumen therethrough that is radially circumscribed by a polymeric outer layer that is bonded thereto. The scope system also has a camera head, coupled to the distal end of the deployment tether. A video camera (or other reflective-photonic optical inspection instrument) is coupled to the camera head, for capturing video images within a camera field of view. The captured images are received within a video control system that is coupled to the camera. In the inspection method, a first internal area of interest within the provided combustion turbine engine is inspected by bending the metallic inner tube to conform elongate profile of the deployment tether to a first deformation profile, which facilitates its insertion with the camera head proximate the first internal area of interest within the power generation machine through a corresponding internal passage. The first deformation profile deployment tether and camera head are inserted into the corresponding power generation machine internal passage, so that the camera head is proximate the first area of interest. The camera field of view is oriented to include the first area of interest therein by moving the deployment tether proximal end, at which time an image is captured with the camera. The captured image is transferred to the video control system. One or more other areas of interest within the turbine engine are respectively inspected by withdrawing the first deformation profile deployment tether and camera head from the power generation machine. Thereafter the deployment tether metallic inner tube is bent, conforming to second or other subsequent deformation profiles, to facilitate insertion of the tether and camera head proximate a second or other subsequent areas of interest within the power generation machine through corresponding internal passages, as was done in the first area of interest inspection. The second or other subsequent deformation profile deployment tether and camera head are inserted into the corresponding internal passage, so that the camera head is proximate the second or other subsequent areas of interest. In the second or subsequent inspection of areas of interest, the camera field of view is oriented to include the respective area of interest therein and a corresponding image is captured. The captured images are transferred to the video control system, as was done with the first captured image. In another embodiment, a deployment tether, having a first deformation profile, and a camera head are inserted into the turbine engine so that the camera head is axially spaced away from a first turbine with the camera field of view including a first area of interest of the first blade. The blade image in the field of view is captured and transferred to the video control system. The turbine rotor is then rotated so that his camera field of view includes a corresponding first area of interest of a second or subsequent turbine blade. Images of each desired blade that is rotated into the camera field of view is captured and transferred to the video control system.

The respective features of the exemplary embodiments of the invention may be applied jointly or severally in any combination or sub-combination.

BRIEF DESCRIPTION OF THE DRAWINGS

The exemplary embodiments of the invention can be understood by considering the following detailed description in conjunction with the accompanying drawings, in which.

To facilitate understanding, identical reference numerals have been used, where possible, to designate identical elements that are common to the figures.

DETAILED DESCRIPTION

Exemplary embodiments of the invention are utilized in non-destructive evaluation optical inspection systems. The system includes video cameras or other reflective-photonic optical instruments, such as laser profilometers or 3D white light laser dimensional scanners, which are incorporated in a camera head. The camera head is coupled to a distal end of a self-supporting and shape-retaining elongate deformable deployment tether. The deployment tether is bendable, for insertion through cavities of power generation machines and orientation of the camera head field of view on the internal area of interest. The deployment tether is capable of being deformed repeatedly, for inspection of different areas of interest. Unlike known rigid tube borescopes, the deformable deployment tether used in embodiments of the invention can be bent to conform to tortuous insertion paths within power generation machinery internal cavities. Unlike known flexible tube borescopes, the deformable deployment tether used in embodiments of the invention is self-supporting, so that the camera field of view remains oriented in a stable position for image capture. In some embodiments, interchangeable camera heads are selectively coupled to the deployment tether, so that a kit or family of different optical inspection instruments are available to carry out multiple types of inspections within a single or multiple types of power generation machinery. In some embodiments described herein, the camera is coupled to a video control system that receives camera or other optical instrument images for further processing, and a non-volatile memory device coupled thereto, for storage of the images. In some embodiments, the video control system includes a personal computer or a tablet computing device or a smart telephone.

Figure 1:
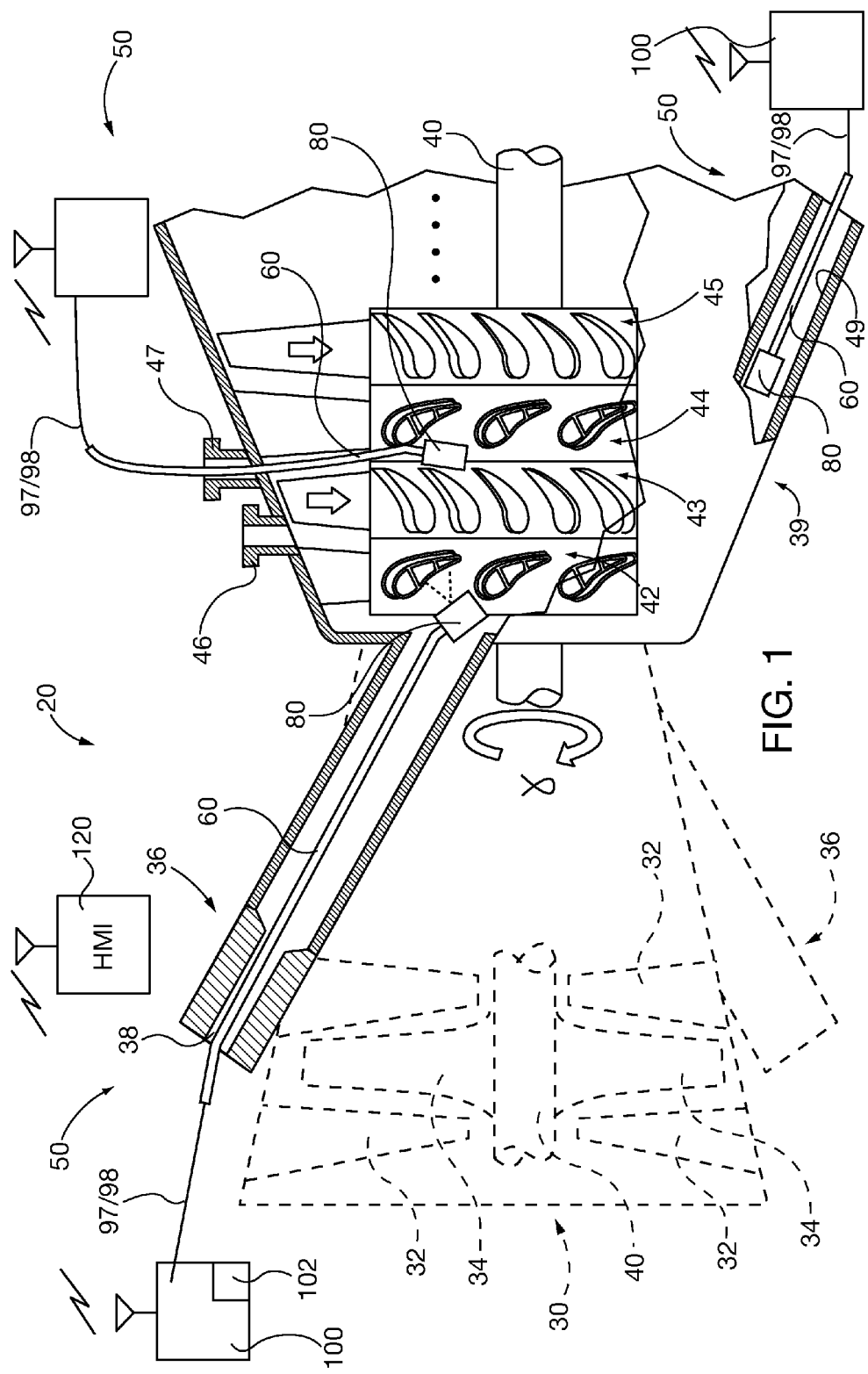
FIG. 1 is a schematic elevational view of exemplary embodiments of an optical inspection system of the invention positioned within cavities of a combustion turbine engine power generation machine.

FIG. 1 is a known combustion turbine engine 20 type of power generation machine, which is also referred to as a gas turbine engine. The engine 20 comprises a compressor section 30, wherein Row 1 stationary vanes 32 and rotating blades 34 are shown in phantom. The compressor section 30 generally includes multiple rows of vanes and blades. The engine combustor section 36 includes a combustor access port 38, such as a combustor pilot/igniter port. The engine 20 further comprises a turbine section 39. A rotating engine shaft 40 mounts the compressor blades (e.g., blades 34) and turbine section blades, such as the Row 1 blades 43 and the Row 2 blades 45. The turbine section 39 also has opposing rows of stationary vanes, such as the Row 1 vanes 42 and Row 2 vanes 44. Cavity space between Row 1 opposing vanes and blades is accessible by one or more circumferentially oriented Row 1 access ports 46 that are in communication with the space. Similarly, one or more circumferentially oriented Row 2 access ports 47 communicates with the space between opposed Row 2 vanes and blades. The engine 20 has one or more cooling air cavities 49, which are accessible from outside the engine. In FIG. 1 a plurality of exemplary video scope inspection systems 50 of the invention are externally inserted into different respective engine 20 cavities, facilitating optical inspection of various desired areas of interest within the engine. The inspection system 50 is also useful for inspecting other types of power generation equipment, such as steam turbine engines, generators, condensation, or other types of associated piping or conduits, or other types of machinery.

Figure 2:
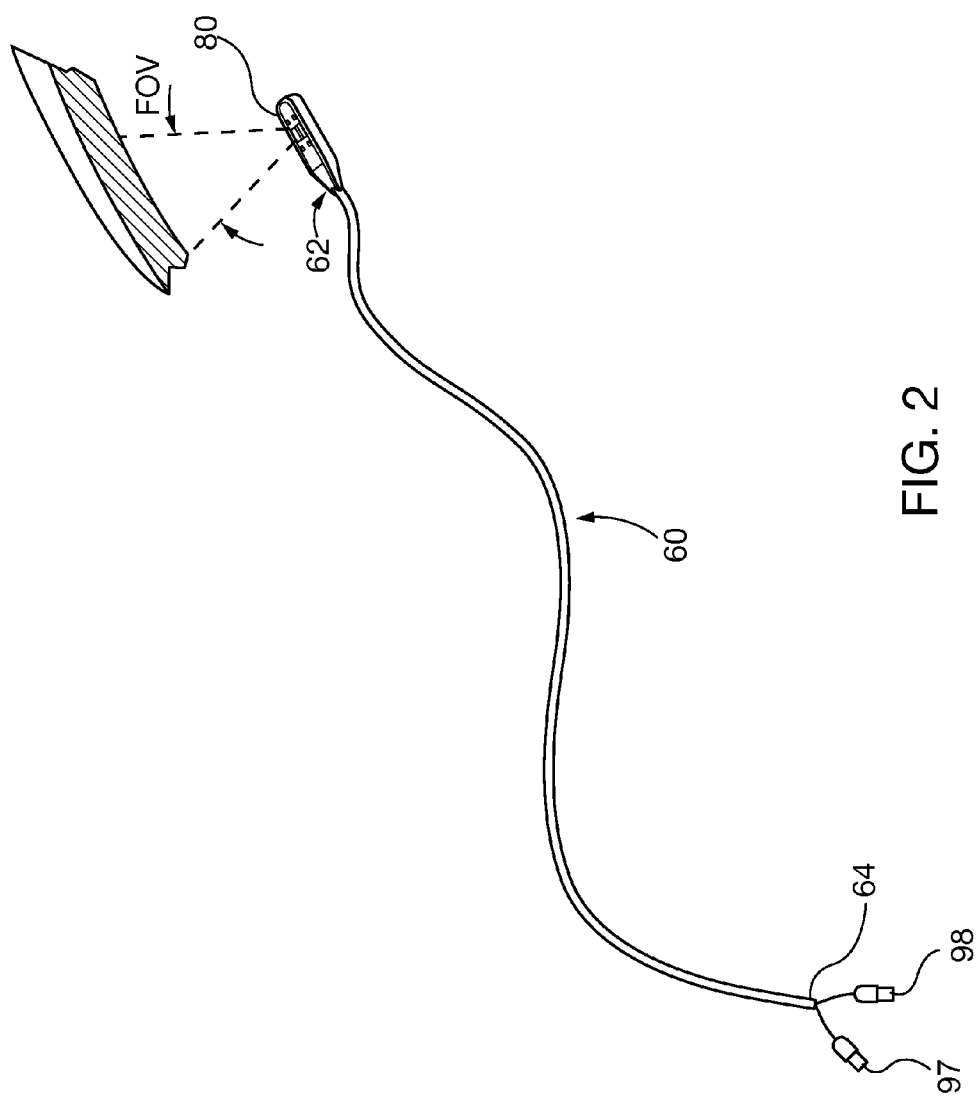
FIG. 2 is a perspective view of an embodiment a deployment tether, camera head and camera being used to inspect an area of interest within a combustion turbine engine power generation machine.

Referring both to FIGS. 1 and 2, the video scope inspection system comprises a deformable, self-supporting deployment tether 60 external the engine 20 that is inserted through a desired inspection port, such as the inspection ports 38, 47 and 49, to an area of interest within the engine. The deployment tether 60 has a distal end 62, that is inserted in the engine 20, to which is coupled a camera head 80. The camera head 80 houses an optical inspection instrument that has a field of view (FOV). The deployment tether has a proximal end 64 that is manipulated external the engine 20, for moving the camera head FOV proximate a desired area of interest within the engine, so that optical images can be obtained for evaluation and inspection.

The deployment tether 60 is deformable by bending, yet once bent is self-supporting, unlike known borescope cable-type tethers or rigid tubular tethers. Thus, the tether 60 is deformable to maneuver through various engine 20 cavities, yet its self-supporting structure allows and maintains desired alignment of the camera head and its coupled optical instrument FOV with the engine internal area of interest. The exemplary deployment tether 60 of FIGS. 1-4 comprises a flexible, metallic inner tubular member 66, over which is applied an adhesive layer 68 and an outer polymeric layer 70. The outer polymeric layer 70 is resilient and relatively softer than components within the turbine engine, thereby reducing likelihood of damage to the engine components upon inadvertent contact with the tether 60 during an inspection procedure. The tether 60 defines a lumen 72 within the tubular member 66 inner diameter. The exemplary deployment tether construction is shown and described in U.S. Pat. No. 4,216,802, the entire contents of which is incorporated by reference herein.

It is also believed that commercially available tubing products incorporating the general construction described in U.S. Pat. No. 4,216,802, including inner tubular members constructed of aluminum tubing material, are sold under SYNFLEX® or DEKABON® trademarks worldwide by hydraulic system supply companies. Generally, such tubing products are marketed as being suitable for hydraulic or other fluid conduits that are bent to a desired shape for permanent installation within an industrial environment. The inventors herein recognized that the properties of such commercial flexible tubing are advantageous for application in optical inspection scope applications, where it is desired to maneuver the camera head through internal passages within the power generation machine. The tubing is bent to a profile matching that of the internal passage, so that the camera head is insertable to the area of interest, with less likelihood of inadvertent contact between the tether 60 and the engine 20 internal components during the insertion procedure. As previously indicated, it is desirable to avoid inadvertent contact between the engine 20 internal components and the tether 60, to reduce risk of engine component damage. However, once bent the tether tubing has sufficient self-supporting structural integrity properties so that the field of view does not shift or otherwise oscillate due to tether self-flexure. In contrast, a flexible borescope tether that is not self-supporting requires abutment of the tether or camera head against an internal support surface (increasing risk of internal component damage from inadvertent contact) and risk of random field of view shift, should the tether inadvertently shift within the engine passage during an inspection procedure.

Figure 3:
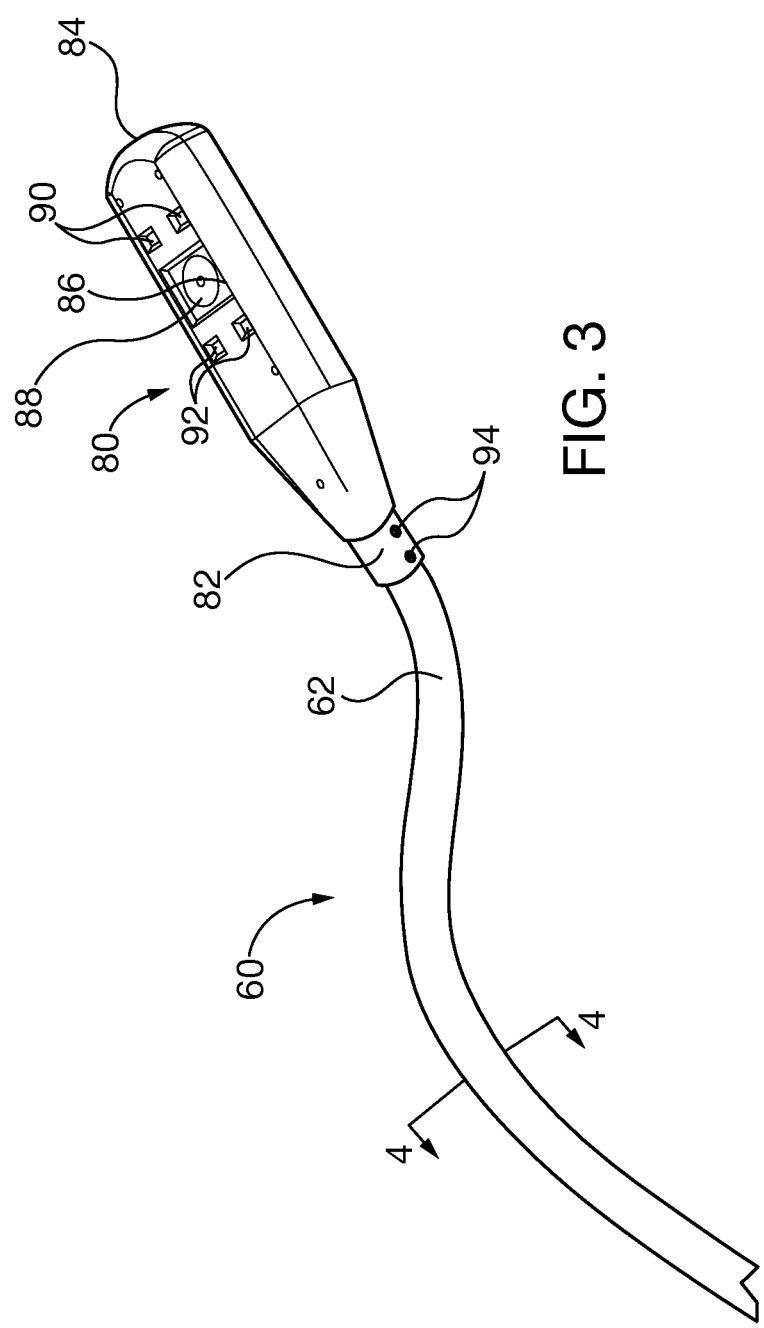
FIG. 3 is a perspective view of the deployment tether and camera head of FIG. 2.
Figure 4:
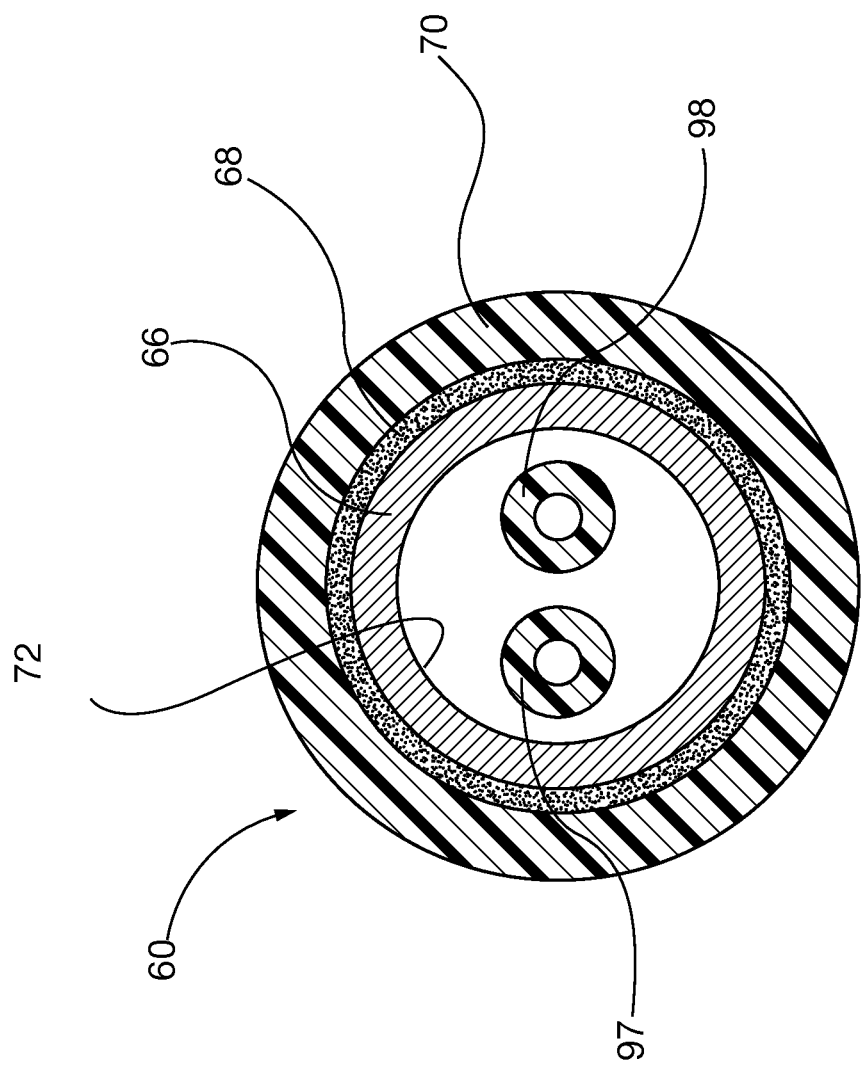
FIG. 4 is a cross section of the deployment tether of FIG. 3, taken along 3-3 thereof.
Figure 5:
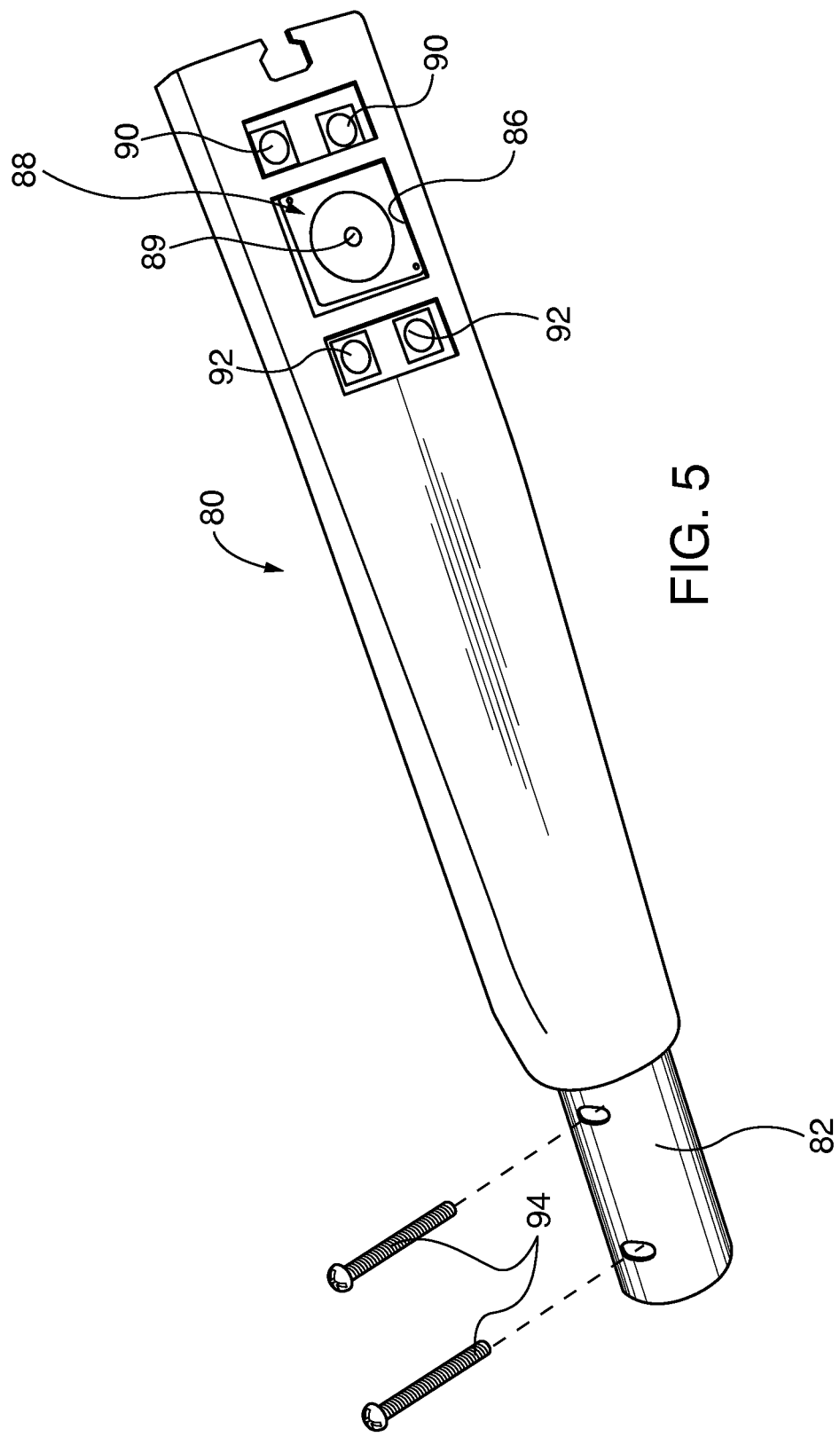
FIG. 5 is a bottom perspective view of the camera head of FIG. 3, including an exemplary computer video camera coupled to and retained therein.
Figure 6:
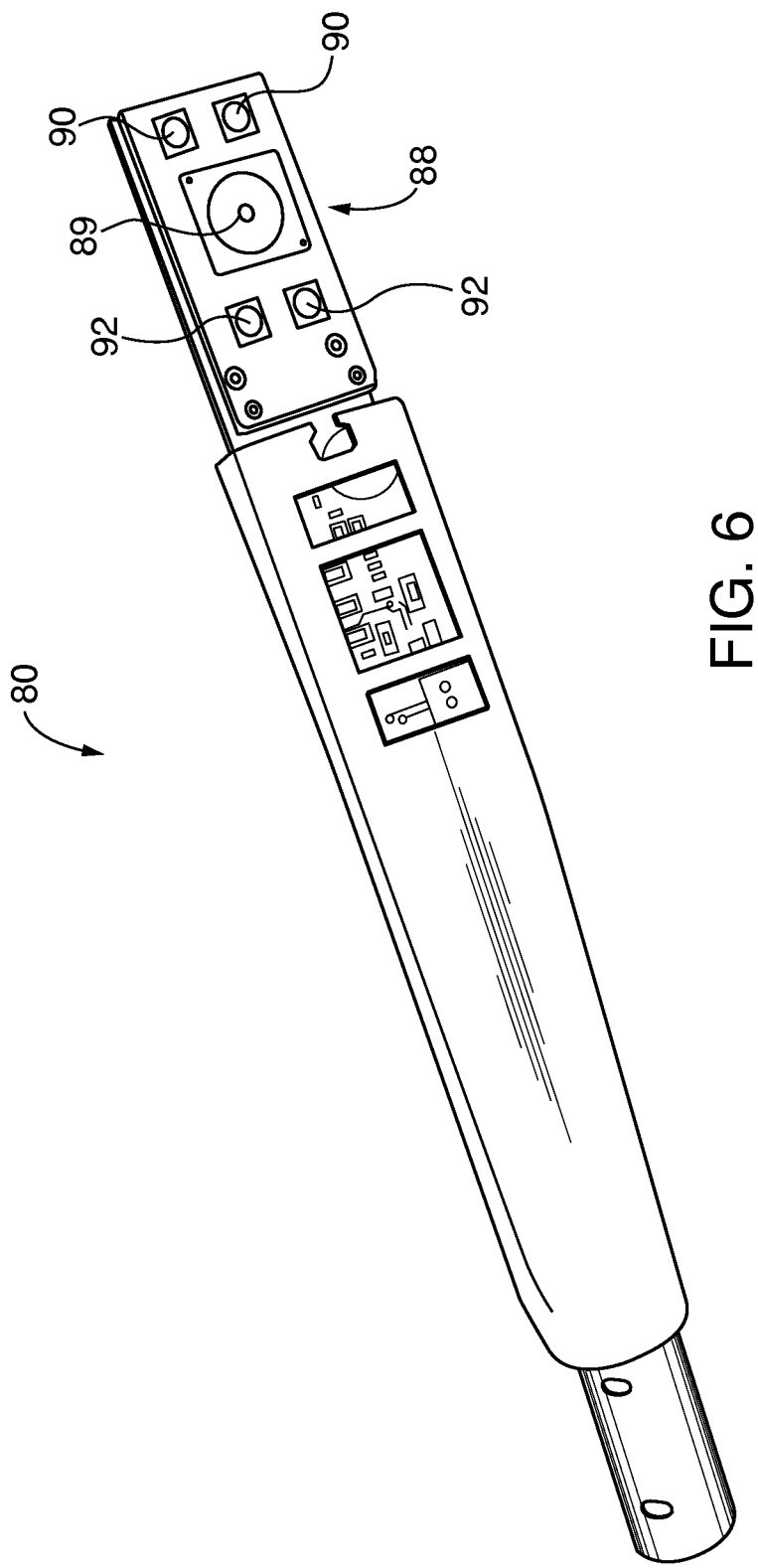
FIG. 6 is a bottom perspective view of the camera head of FIG. 6 with a partially-removed computer video camera.

The camera head 80 structure is shown in FIGS. 3, 5, and 6. The camera head 80 has a camera head tether coupler 82 on its proximal end and a removable distal cap or tip 84 on its distal end. A viewing aperture 86 allows optical communication between an internally coupled optical instrument, such as a video camera 88 and its camera lens 89. The exemplary optical instrument video camera 88 of FIG. 6 is a commercially available, five mega pixel (5 MP) or greater personal computer, tablet computing device, or smart telephone camera board that also incorporates one or more illumination devices, such as light emitting diode (LED) pairs 90, 92. The camera head also defines apertures for transmission of the LED output light to illumination the camera FOV. Other types of photonic non-destructive evaluation instruments can be substituted for the video camera 88, such as video or still cameras, laser profilometers or 3-D laser scanners, such as those described in previously referenced, co-pending U.S. patent application Ser. No. 13/972,000, filed, Aug. 21, 2013 and the previously referenced, copending United States utility patent application entitled "Method And System For Surface Profile Inspection Of Off-Line Industrial Gas Turbines And Other Power Generation Machinery", assigned Ser. No. 14/732,982.

The camera head tether coupler 82 is selectively or permanently coupled to the tether distal end 62 with one or elongated fasteners 94, such as self-tapping screws, rivets, solid pins, roll pins. In some embodiments plural fasteners 94 are in parallel, orthogonal or skewed relative alignment. Selectively releasable couplings, such as pipe threaded fittings (e.g., a male threaded pipe fitting coupled to the tether distal end 62 and mating female threads in the camera head tether coupler 82), or bayonet mounts, are substituted for the elongated fasteners 94 in some embodiments.

The camera head 80 structure of FIGS. 5 and 6 incorporates an internal passage for coupling receipt of the camera 88 or other optical instrument. The camera head cap 84 is removed from the camera head 80, allowing sliding insertion, and retention of the camera 88 therein, so that the camera lens 89 is in optical communication with the camera head exterior, as are the LEDs 90, 92. In some embodiments, the camera head 80 and cap 84 are constructed of polymeric material, with the internal passage configured to receive one or more types of optical instruments, such as the video camera 88. In this manner, a single head design can accommodate different types of optical instruments by substituting them for different types of inspections. Polymeric material construction reduces likelihood of inadvertent contact damage to engine 20 internal components, as was previously described in connection with the deployment tether 60, construction. In some embodiments the camera head 80 and its cap 84 are formed with a 3D printer, so that a design created on a computer assisted drawing work station is quickly formed into a working camera head.

Figure 7:
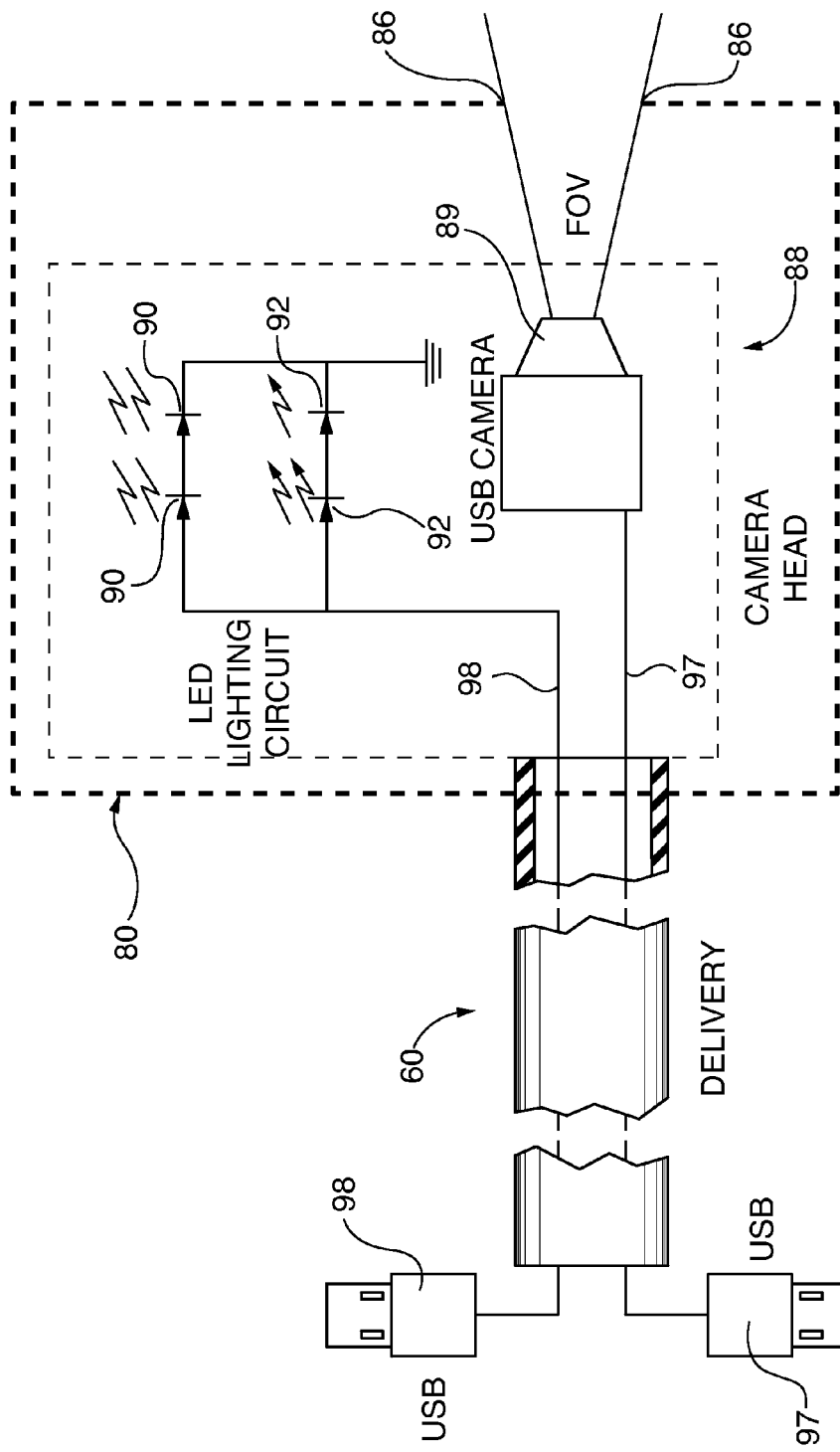
FIG. 7 is a block diagram of an exemplary embodiment of the inspection system of the invention.

As shown in FIGS. 1 and 7, the camera (here a self-contained, modular computer camera board 88 with incorporated illumination LED pairs 90, 92) or other optical instrument is coupled to camera USB cable 97 and lighting system USB cable 98, with the male ends of both USB cables in turn coupled to a video control system 100 that is located external of the inspected power generation machine. In some embodiments a common, single USB cable couples the lighting system and the camera to the video control system. In some embodiments, the video control system is a commercially available personal computer, or a tablet computing device, or a smart telephone that includes a processor capable of executing software, for receiving camera video images for further processing, and for storing camera images in a non-volatile memory device 102 that is coupled thereto. In some embodiments, the stored or live images in some embodiments are remotely accessible, such as through a wireless communication accessible, human-machine interface (HMI) in a tablet computing device 120 or smart telephone, or via an Internet communications pathway that is in communication with the video control system 100.

While reference to an exemplary video control system 100 architecture and implementation by software modules executed by its processor, it is also to be understood that exemplary embodiments of the invention may be implemented in various forms of hardware, software, firmware, special purpose processors, or a combination thereof. Preferably, aspects of the invention embodiments are implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may be either part of the microinstruction code or part of the program (or combination thereof) which is executed via the operating system. In addition, various other peripheral devices may be connected to the computer/controller platform.

It is to be understood that, because some of the constituent system components and method steps depicted in the accompanying figures are preferably implemented in software, the actual connections between the system components (or the process steps) may differ depending upon the manner in which the exemplary embodiments are programmed. Specifically, any of the computer platforms or devices may be interconnected using any existing or later-discovered networking technology and may all be connected through a lager network system, such as a corporate network, metropolitan network or a global network, such as the Internet.

In some embodiments, the video scope inspection system 50 comprises a kit of modular components that are selectively mixed and matched to perform a desired optical inspection. A plurality of reusable deployment tethers, of various outer diameters, stiffness and/or lengths are provided, for meeting the needs of different types of inspection procedures on different types of power generation equipment. For example, the deployment tether 60 inserted in the combustor inspection port 30 of FIG. 1 is being used to perform a visual inspection of the turbine section Row 1 vanes 42. Due to the relatively long extension into the engine, a longer, stiffer, and larger diameter deployment tether might be necessary for this vane 42 inspection as compared to the tether 60 that is inserted into the turbine section internal cavity 49. The internal cavity 49 is of shorter length and has a more tortuous, insertion path than the insertion path through the combustor port 38. Therefore, the tether 60 for the internal cavity 49 insertion may require a shorter tether length, smaller diameter, and easier bending capability than one chosen for a combustor port 38 insertion path to the vane 42.

An exemplary method for performing an internal nondestructive inspection of areas of interest within a power generation machine (e.g., engine 20) is now described, though it should be understood that similar inspections could be performed on other types of power generation equipment. Referring to FIG. 1, the provided turbine engine 20 has areas of interest therein that are in communication with corresponding internal passages, 38, 47 and 49. The passages are externally accessible from outside the engine 20. A video inspection scope system 50 is provided, which includes a self-supporting and shape-retaining, elongate deformable tubular deployment tether 60 having distal and proximal ends. The tether is constructed of a metallic inner tube 66, defining a lumen 72 therethrough, which is radially circumscribed by a polymeric outer layer 70 that is bonded thereto. A camera head 80 is coupled to the distal end 62 of the deployment tether 60. A video camera 88 (or other reflective-photonic, optical inspection instrument), is coupled to the camera head 80, for capturing video images within a camera field of view (FOV). A video control system 100 is coupled to the video camera 88, and receives camera video images for further processing. During the inspection process, a first internal area of interest is inspected within the provided power generation machine by bending the metallic inner tube 66 to conform elongate profile of the deployment tether 60 to a first deformation profile. The bent first profile facilitates insertion of the tether and camera head proximate the first internal area of interest through a corresponding internal passage that is in communication with the area of interest. The first deformation profile deployment tether and camera head are inserted into the corresponding internal passage, so that the camera head is proximate the first area of interest. Movement of the deployment tether proximal end 64 orients the camera field of view to include the first area of interest, and an image of the area of interest is captured by the camera. The captured image is transferred to the video control system, 100.

An additional exemplary embodiment of the invention, shown in FIG. 1, features a method for internal nondestructive inspection of multiple areas of interest within a combustion turbine engine 20 by sequential multiple insertions, inspections and retraction of the video inspection scope system 50. A first internal area of interest within the provided combustion turbine engine 20 is inspected by bending the metallic inner tube 66 to conform elongate profile of the deployment tether 60 to a first deformation profile, e.g. through port 47, which facilitates its insertion with the camera head proximate the Row 2 vanes 44, which is the first internal area of interest. The first deformation profile deployment tether 60 and camera head 80 are inserted into the Row 2 inspection port 47, so that the camera head 80 is proximate the Row 2 vane 44. The camera 88 field of view is oriented to include the first area of interest therein by moving the deployment tether proximal end, at which time an image is captured with the camera. The captured image is transferred to the video control system 100. One or more other areas of interest within the turbine engine (e.g., the cavity 49 or the Row 1 vanes 42) are respectively inspected by withdrawing the deployment tether 60 in its first deformation profile, and camera head 80 from the Row 2 inspection port 47. Thereafter, the deployment tether metallic inner tube 66 is re-bent to conform its elongate profile to a second or other subsequent deformation profiles, to facilitate insertion of the tether 60 and camera head 80 proximate a second or other subsequent areas of interest within the power generation machine through corresponding internal passages (e.g., ports 38 or 46), as was done in the first area of interest inspection. The second or other subsequent deformation profile deployment tether and camera head are inserted into the corresponding internal passage, so that the camera head is proximate the second or other subsequent areas of interest. In the second or subsequent inspection of areas of interest, the camera field of view is oriented to include the respective area of interest therein and a corresponding image is captured. The captured images are transferred to the video control system, as was done with the first captured image.

In another exemplary inspection embodiment shown in FIG. 1, a deployment tether 60, having a first deformation profile, and a camera head are inserted into the turbine engine port 47, so that the camera head is axially spaced away from a trailing edge of a first turbine blade 43 in the engine Row 1, with the camera field of view including a first area of interest of the first blade. The blade image in the field of view is captured and transferred to the video control system 100. The turbine rotor 40 is then rotated so that the camera field of view includes a corresponding first area of interest of a second or subsequent turbine blade. Images of each desired blade that is rotated into the camera field of view is captured and transferred to the video control system 100.

Although various embodiments that incorporate the invention have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the phraseology and terminology used herein is tar the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted", "connected", "supported" and "coupled" and variations thereof have been used broadly, and have encompassed direct and indirect mountings, connections, supports, and couplings. Further, "connected" and "coupled" are not restricted to physical, mechanical, or electrical connections or couplings.

What is claimed is:

1. A video inspection system, comprising:
a self-supporting and shape-retaining, elongate deformable tubular deployment tether having distal and proximal ends, the tether constructed of a metallic inner tube, defining a lumen therethrough, that is radially circumscribed by a polymeric outer layer that is bonded thereto;
a camera head, coupled to the distal end of the deployment tether;
a five mega pixel (5 MP) or greater personal computer, tablet computing device, or smart telephone video camera board, coupled to the camera head and a USB-type cable retained within the tube lumen, for capturing video images;
a video control system, coupled to the video camera board, via the USB-type cable, for receiving camera video images for further processing, and a non-volatile memory device coupled thereto, for storage of camera video images; the video control system including a personal computer or a tablet computing device or a smart telephone;
a selectively engageable coupling element coupled to the deployment tether distal end and the camera head, for selectively engaging the tether and camera head to each other; and
a plurality of additional, replaceable camera heads respectively having different reflective-photonic, non-destructive evaluation instruments coupled thereto.

2. The system of claim 1, the respective different reflective-photonic, non-destructive evaluation instruments comprising video or still cameras, laser profilometers, or 3-D laser scanners.

3. The system of claim 1, the deployment tether comprising a deformable metallic inner tube capable of multiple, sequential bending deformations along a common portion of said tube without cracking the inner tube.

4. The system of claim 3, the deformable metallic inner tube comprising aluminum material.

5. A method for internal non-destructive inspection of areas of interest within a power generation machine, comprising:
providing a power generation machine, having areas of interest therein that are in communication with corresponding internal passages, which passages are externally accessible from outside the machine;
providing a video inspection scope system, including:
a self-supporting and shape-retaining, elongate deformable tubular deployment tether having distal and proximal ends, the tether constructed of a metallic inner tube, defining a lumen therethrough, that is radially circumscribed by a polymeric outer layer that is bonded thereto;
a camera head, coupled to the distal end of the deployment tether;
a video camera coupled to the camera head, for capturing video images within a camera field of view; and
a video control system, coupled to the video camera, for receiving camera video images for further processing;
inspecting a first internal area of interest within the provided power generation machine by:
bending the metallic inner tube to conform elongate profile of the deployment tether to a first deformation profile, to facilitate insertion of the tether and camera head proximate the first internal area of interest within the power generation machine through a corresponding internal passage that is in communication therewith;
inserting the first deformation profile deployment tether and camera head into the corresponding power generation machine internal passage, so that the camera head is proximate the first area of interest;
moving the deployment tether proximal end, orienting the camera field of view to include the first area of interest therein, and capturing an image thereof with the camera; and
transferring the camera captured image of the first area of interest to the video control system.

6. The method of claim 5, further comprising:
withdrawing at least a portion of the first deformation profile deployment tether and camera head from the power generation machine;
bending the metallic inner tube to conform elongate profile of the deployment tether to a second deformation profile, to facilitate insertion of the tether and camera head proximate a second area of interest within the power generation machine through a corresponding internal passage that is in communication therewith;
inserting the second deformation profile deployment tether and camera head into the corresponding power generation machine internal passage, so that the camera head is proximate the second area of interest;
orienting the camera field of view to include the second area of interest therein and capturing an image thereof with the camera; and
transferring the camera captured image of the second area of interest to the video control system.

7. The method of claim 5, further comprising sequentially deforming a common section of said metallic inner tube during one or more power generation machine internal inspections without cracking the inner tube.

8. The method of claim 5, the provided power generation machine comprising a combustion turbine engine, or a steam turbine engine, or a generator.

9. The method of claim 5, the provided video camera comprising a five mega pixel (5 MP) or greater personal computer, tablet computing device, or smart telephone camera board that is coupled to the video control system via a USB-type cable retained within the tube lumen.

10. The method of claim 9, further comprising:
the provided video scope system further having:
a selectively engageable a selectively engageable coupling element coupled to the deployment tether distal end and the camera head, for selectively engaging the tether and camera head to each other, and
a plurality of additional, replaceable camera heads respectively having different reflective-photonic, non-destructive evaluation instruments coupled thereto; and
selectively changing camera heads prior to inspecting one or more areas of interest within one or plural power generation machines.

11. The method of claim 10, the respective provided different reflective-photonic, non-destructive evaluation instruments comprising video or still cameras, laser profilometers, or 3-D laser scanners.

12. The method of claim 11, the video control system receiving images from the reflective-photonic non-destructive instruments by a wireless signal transmission system.

13. The method of claim 5, the provided video control system comprising a personal computer, tablet computing device, or smart telephone and a non-volatile memory device coupled thereto, for storage of camera video images.

14. The method of claim 13, the provided video control system receiving images from the video camera by a wireless signal transmission system.

15. A method for internal non-destructive inspection of areas of interest within a combustion turbine engine, comprising:
providing a combustion turbine engine having:
compressor and turbine sections including therein a rotatable rotor with rows of blades affixed thereto, and rows of stationary vanes interposed between the blade rows;
a combustor section interposed between the compressor and turbine sections; and
respective internal passages that are in communication with internal areas of interest within the respective compressor, turbine and combustor sections, the passages externally accessible from outside the engine;
providing a video inspection scope system, having
a self-supporting and shape-retaining, elongate deformable tubular deployment tether having distal and proximal ends, the tether constructed of a metallic inner tube, defining a lumen therethrough, that is radially circumscribed by a polymeric outer layer that is bonded thereto;
a camera head, coupled to the distal end of the deployment tether;
a video camera coupled to the camera head, for capturing video images within a camera field of view; and
a video control system, coupled to the video camera, for receiving camera video images for further processing;
inspecting a first internal area of interest within the provided combustion turbine engine by:
bending the metallic inner tube to conform elongate profile of the deployment tether to a first deformation profile, to facilitate insertion of the tether and camera head proximate the first internal area of interest within the power generation machine through a corresponding internal passage that is in communication therewith;
inserting the first deformation profile deployment tether and camera head into the corresponding power generation machine internal passage, so that the camera head is proximate the first area of interest;
moving the deployment tether proximal end, orienting the camera field of view to include the first area of interest therein, and capturing an image thereof with the camera;
transferring the camera captured image of the first area of interest to the video control system; and
inspecting one or more other areas of interest within the turbine engine, respectively by:
withdrawing the first deformation profile deployment tether and camera head from the power generation machine;
bending the metallic inner tube to conform elongate profile of the deployment tether to a second or other subsequent deformation profiles, to facilitate insertion of the tether and camera head proximate a second or other subsequent areas of interest within the power generation machine through corresponding internal passages that are in communication therewith;
inserting the second or other subsequent deformation profile deployment tether and camera head into the corresponding internal passage, so that the camera head is proximate the second or other subsequent areas of interest;
orienting the camera field of view to include the second or other subsequent areas of interest therein and capturing a corresponding image thereof with the camera; and
transferring the camera captured image of the second or other subsequent areas of interest to the video control system.

16. The method of claim 15, further comprising inspecting a row of turbine blades by:
inserting a first deformation profile deployment tether and camera head into the turbine engine so that the camera head is axially spaced away from a first turbine blade with the camera field of view including a first area of interest of the first blade, capturing a corresponding image thereof with the camera and transferring the corresponding image to the video control system;
rotating the turbine rotor so that the camera field of view includes a corresponding first area of interest of a second or subsequent turbine blade, capturing and transferring corresponding images thereof to the video control system; and inspecting other areas of interest within the turbine engine.

* * * * *